United States Patent
Takematsu et al.

[11] Patent Number: 5,510,317
[45] Date of Patent: Apr. 23, 1996

[54] N-ACYL-N-PHENYLMALEAMIC ACID DERIVATIVES, METHODS OF PRODUCING SAME, AND HERBICIDES CONTAINING SAME AS EFFECTIVE COMPONENTS

[75] Inventors: Tetsuo Takematsu, Utsunomiya; Takashi Kume; Takeo Komata, both of Kawagoe; Kiyoshi Suzuki, Utsunomiya; Yukio Ikeda, Kawachi; Matsue Kawamura; Kaoru Mori, both of Kawagoe, all of Japan

[73] Assignee: Central Glass Co. Ltd., Ube, Japan

[21] Appl. No.: 256,683

[22] PCT Filed: Dec. 2, 1993

[86] PCT No.: PCT/JP93/01755

§ 371 Date: Jul. 20, 1994

§ 102(e) Date: Jul. 20, 1994

[87] PCT Pub. No.: WO94/12468

PCT Pub. Date: Jun. 9, 1994

[30] Foreign Application Priority Data

Dec. 2, 1992 [JP] Japan ..................... 4-323469

[51] Int. Cl.$^6$ ............... A01N 27/00; A01N 29/04; A01N 29/10; C07C 229/36
[52] U.S. Cl. ............... 504/147; 560/43; 562/433; 562/457
[58] Field of Search ............... 560/43; 562/433, 562/457; 504/147

[56] References Cited

FOREIGN PATENT DOCUMENTS 0496900  8/1992  European Pat. Off. .
46-10526  3/1971  Japan .
1-49140  10/1989  Japan .

*Primary Examiner*—José G. Dees
*Assistant Examiner*—Joseph M. Conrad, III
*Attorney, Agent, or Firm*—Keck, Mahin & Cate

[57] ABSTRACT

The invention provides N-acyl-N-phenylmaleamic acid derivatives represented by the general formula [I], a method of producing the same, and a herbicide containing the same as the effective components,

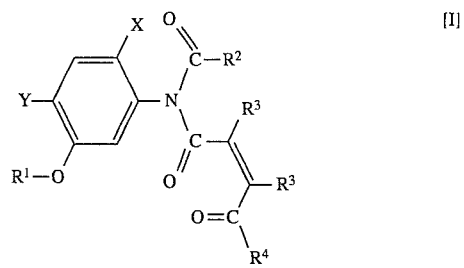

wherein X and Y each individually represent hydrogen atoms or halogen atoms, $R^1$ represents a hydrogen atom, a halogen atom, a lower alkyl group, a lower alkenyl group, a lower alkynyl group, a lower alkoxyalkyl group or a lower alkoxycarbonylalkyl group, $R^2$ represents a lower alkyl group, a halogenated lower alkyl group or a substituted or unsubstituted phenyl group, $R^3$ represents a hydrogen atom or a lower alkyl group, and $R^4$ represents a hydroxyl, a lower alkoxy group, a lower alkenyloxy group, a lower alkynyloxy group, a lower alkoxyalkoxy group, a benzyloxy group or a lower alkoxycarbonylalkoxy group. This herbicide which is very useful can be widely applied to upland, paddy field, orchard, turf, forest, non-crop land, etc., and is not harmful to crops.

9 Claims, No Drawings

N-ACYL-N-PHENYLMALEAMIC ACID DERIVATIVES, METHODS OF PRODUCING SAME, AND HERBICIDES CONTAINING SAME AS EFFECTIVE COMPONENTS

[TECHNOLOGICAL FIELD]

The present invention relates to herbicides, and more particularly to N-acyl-N-phenylmaleamic acid derivatives which are novel compounds, to methods of producing the same and to herbicides containing the same as the effective components. N-acyl-N-phenylmaleamic acid derivatives of the present invention exhibit excellent herbicidal activity. The derivatives are useful as a herbicide which can be widely applied to upland, paddy field, orchard, pasture, turf, forest, non-crop land, etc. The derivatives are not harmful to crops.

[BACKGROUND TECHNOLOGY]

Hitherto, herbicidal activity of maleamic acid derivatives has not been reported in large numbers.

It is an object of the present invention to provide N-acyl-N-phenylmateamic acid derivatives as novel compounds exhibiting excellent herbicidal activity against various very harmful weeds and not being harmful to crops, methods of producing the same and herbicides containing the same as the effective components.

[DISCLOSURE OF THE INVENTION]

The inventors have found that novel maleamic acid derivatives each having a specific substituent acyl group or substituent aryl group bonded to an amide nitrogen atom are very excellent in herbicidal activity, selectivity and herbicidal spectrum, and completed the present invention.

The present invention provides N-acyl-N-phenylmaleamic acid derivatives represented by the general formula [I], methods of producing the same, and herbicides containing the same as the effective components:

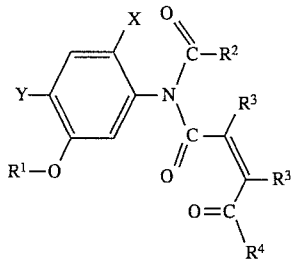

[I]

wherein X and Y each individually represent hydrogen atoms or halogen atoms, $R^1$ represents a hydrogen atom, a halogen atom, a lower alkyl group, a lower alkenyl group, a lower alkynyl group, a lower alkoxyalkyl group or a lower alkoxycarbonylalkyl group, $R^2$ represents a lower alkyl group, a halogenated lower alkyl group or a substituted or unsubstituted phenyl group, $R^3$ represents a hydrogen atom or a lower alkyl group, and $R^4$ represents a hydroxyl, a lower alkoxy group, a lower alkenyloxy group, a lower alkynyloxy group, a lower alkoxyalkoxy group, a benzyloxy group or a lower alkoxycarbonylalkoxy group.

N-acyl-N-phenylmaleamic acid derivatives [I] as compounds of the present invention can be synthesized, for example, by the following methods.

[SYNTHESIS METHOD (a)]

N-acyl-N-phenylmaleamic acid derivatives [I] which are compounds of the present invention can be synthesized by reacting imidoylchloride derivatives represented by the general formula [II] with carboxylic acids represented by the general formula [III], without using any solvent or in a suitable solvent such as benzene, toluene, xylene, methylene chloride, chloroform, ethyl acetate, dioxane, tetrahydrofuran, diethylether, N,N-dimethylformamide or dimethyl sulfoxide, with the addition of a suitable deacidifying agent such as an organic base such as triethylamine or pyridine or an inorganic base such as potassium hydroxide or sodium hydroxide.

The reaction temperature is usually from −20° C. to 250° C. and preferably from 0° C. to 100° C.

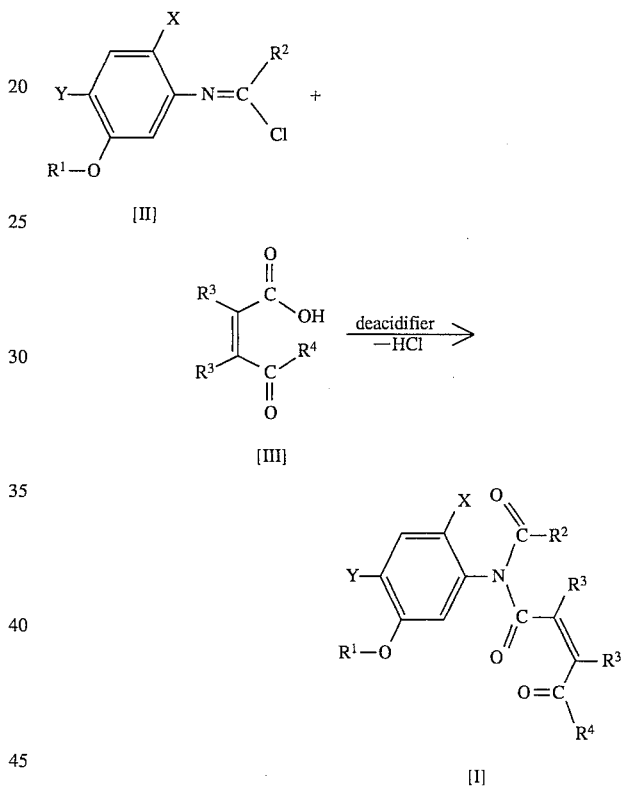

wherein X and Y each individually represent hydrogen atoms or halogen atoms, $R^1$ represents a hydrogen atom, a halogen atom, a lower alkyl group, a lower alkenyl group, a lower alkynyl group, a lower alkoxyalkyl group or a lower alkoxycarbonylalkyl group, $R^2$ represents a lower alkyl group, a halogenated lower alkyl group or a substituted or unsubstituted phenyl group, $R^3$ represents a hydrogen atom or a lower alkyl group, and $R^4$ represents a hydroxyl, a lower alkoxy group, a lower alkenyloxy group, a lower alkynyloxy group, a lower alkoxyalkoxy group, a benzyloxy group or a lower alkoxycarbonylalkoxy group.

[SYNTHESIS METHOD (b)]

N-acyl-N-phenylmaleamic acid derivatives [I] which are compounds of the present invention can be synthesized by reacting imidoylchloride derivatives represented by the general formula [II] with alkali metal salts [III'] of carboxylic acids represented by the general formula [III], without using any solvent or in a suitable solvent such as benzene, toluene, xylene, methylene chloride, chloroform, ethyl acetate, dioxane, tetrahydrofuran, diethylether, N,N-dimethylformamide, dimethyl sulfoxide or water, if necessary with the addition of a phase transfer catalyst such as a quaternary ammonium salt.

The reaction temperature is usually from 0° C. to 200° C. and preferably from 0° C. to 100° C.

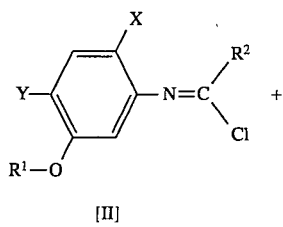

[II]

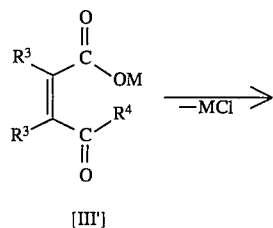

[III']

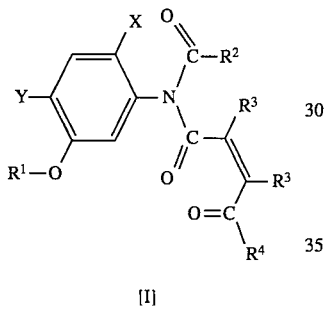

[I]

wherein X and Y each individually represent hydrogen atoms or halogen atoms, $R^1$ represents a hydrogen atom, a halogen atom, a lower alkyl group, a lower alkenyl group, a lower alkynyl group, a lower alkoxyalkyl group or a lower alkoxycarbonylalkyl group, $R^2$ represents a lower alkyl group, a halogenated lower alkyl group or a substituted or unsubstituted phenyl group, $R^3$ represents a hydrogen atom or a lower alkyl group, $R^4$ represents a hydroxyl, a lower alkoxy group, a lower alkenyloxy group, a lower alkynyloxy group, a lower alkoxyalkoxy group, a benzyloxy group or a lower alkoxycarbonylalkoxy group, and M represents an alkali metal.

[SYNTHESIS METHOD (c)]

N-acyl-N-phenylmaleamic acid derivatives [I] which are compounds of the present invention can be synthesized as follows, too.

At first, imidoylchloride derivatives represented by the general formula [II] are obtained as intermediate products by reacting a dehydrochlorinating agent such as polymer-carried triphenylphosphine and carbon tetrachloride with anilide derivatives represented by the general formula [IV], without using any solvent or in a solvent such as methylene chloride, chloroform, benzene, toluene, xylene, ethyl acetate, ether, dioxane, tetrahydrofuran, N,N-dimethylformamide, N,N-dimethylacetamide, dimethyl sulfoxide or sulforan, at a temperature ranging from 0° C. to 200° C. and preferably from 0° C. to 100° C.

Then, after the isolation and purification of the obtained imidoylchloride derivatives represented by the general formula [II] or without the isolation and purification thereof, carboxylic acids represented by the general formula [III] and a suitable deacidifying agent such as an organic base such as triethylamine or pyridine or an inorganic base such as potassium hydroxide or sodium hydroxide are added thereto and reacted therewith, without using any solvent or in a solvent such as methylene chloride, chloroform, benzene, toluene, xylene, cumene, ethyl acetate, ether, dioxane, tetrahydrofuran, N,N-dimethylformamide, N,N-dimethylacetamide, dimethyl sulfoxide, sulfolane, acetone or methylethylketone, at a temperature ranging from −20 C. to 250° C. and preferably from 0° C. to 100° C., thereby synthesizing N-acyl-N-phenylmaleamic acid derivatives [I] which are compounds of the present invention.

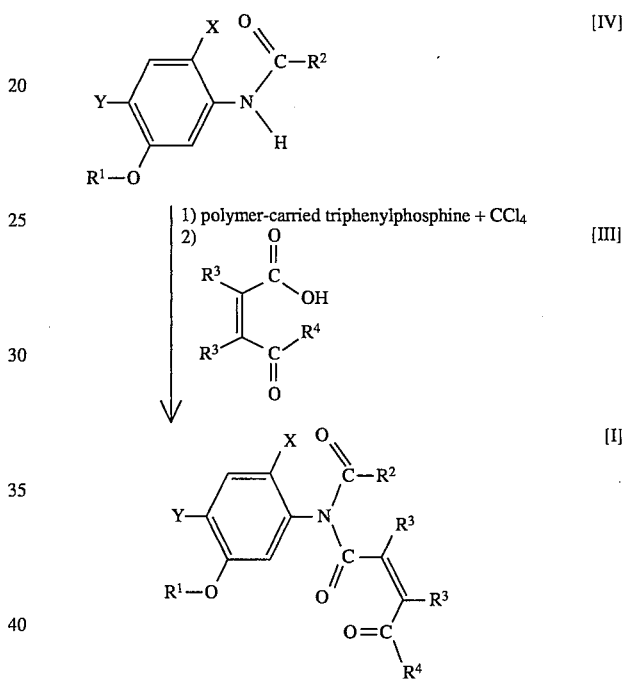

wherein X and Y each individually represent hydrogen atoms or halogen atoms, $R^m$ represents a hydrogen atom, a halogen atom, a lower alkyl group, a lower alkenyl group, a lower alkynyl group, a lower alkoxyalkyl group or a lower alkoxycarbonylalkyl group, $R^2$ represents a lower alkyl group, a halogenated lower alkyl group or a substituted or unsubstituted phenyl group, $R^3$ represents a hydrogen atom or a lower alkyl group, and $R^4$ represents a hydroxyl, a lower alkoxy group, a lower alkenyloxy group, a lower alkynyloxy group, a lower alkoxyalkoxy group, a benzyloxy group or a lower alkoxycarbonylalkoxy group.

As preferable examples of the dehydrochlorinating agent used in the reaction, phosphorus pentachloride, phosphorus trichloride-chlorine, thionyl chloride, arylsulfonylchloride, phosgene, and triphenylphosphine-carbon tetrachloride can be cited as well as the above-mentioned polymer-carried triphenylphosphine-carbon tetrachloride.

As preferable examples of the solvent used in the reaction, halogenated hydrocarbons such as dichloroethane, carbon tetrachloride, chloroform and methylene chloride, aromatic hydrocarbons such as benzene, toluene, xylene and chlorobenzene, and polar solvents such as acetonitrile and dimethyl sulfoxide can be cited.

Imidoylchloride derivatives represented by the general formula [II] as a raw material for the synthesis of N-acyl- N-phenylmaleamic acid derivatives [I] which are compounds of the present invention can be easily synthesized in accordance with the specification of JP-A 4-803407.

[THE BEST MODE TO CARRY OUT THE INVENTION]

Hereinafter, the present invention will be described concretely with reference to Examples.

EXAMPLE 1

Synthesis of N-benzoyl-N-(2-fluoro-4-chloro-5-methoxyphenyl)-2,3-dimethylmaleamic acid methyl ester (A compound which is represented by No. 3 in Table 1 and by the general formula [I].

1.57g (6.63 mmol) of N-(2-fluoro-4-chloro-5-methoxy) phenylbenzimidoylchloride and 1.30 g (6.63 mmol) of 2,3dimethylmaleic acid monomethyl ester potassium salt were mixed in 10 ml of N,N-dimethylformamide, and the stirring under heat was continued for 1 hr at 60° C. After letting the mixture stand to cool the same, it was poured into iced water, and then the organic layer was separated therefrom three times with benzene. The combined organic layer was washed first with water and then with saturated brine. Then, in was dried by using anhydrous magnesium sulfate. Volatile constituents were distilled out under reduced pressure, and then methanol was added to the residue. The precipitate was filtered out. The filtrate was concentrated, and then methanol was again added thereto. Then, it was allowed to stand in a refrigerator. The precipitated crystals were filtered out, thereby to obtain 0.72 g of N-benzoyl-N-(2-fluoro-4-chloro-5-methoxyphenyl) -2,3-dimethyl-maleamic acid methyl ester. The melting point was 142°–145° C.

Table 1 shows N-acyl-N-phenylmaleamic acid derivatives [I] which are compounds of the present invention and their melting points, each of which was obtained by a process analogous to the above process, and Table 2 shows $^1$H-NMR absorption spectrum values thereof. However, the compounds of the present invention are not limited to these.

The compound Nos. in Tables 1 and 2 will be employed in the following examples and experiments.

TABLE 1

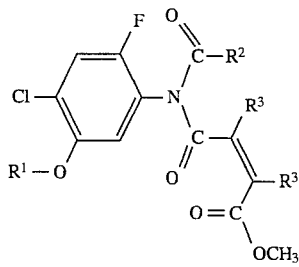

| Compound No. | R$^1$ | R$^2$ | R$^3$ | m.p. (°C.) |
|---|---|---|---|---|
| 1 | —CH$_3$ | —CH$_3$ | —H | 88–89 |
| 2 | —CH$_3$ | —CH$_3$ | —CH$_3$ | 104–106 |
| 3 | —CH$_3$ | —Ph | —CH$_3$ | 142–145 |
| 4 | —CHC≡CH<br>\|<br>CH$_3$ | —CH$_3$ | —CH$_3$ | 106–108 |

TABLE 2

| Compound No. | $^1$H-NMR Absorption Spectrum Values δ (ppm, CDCl$_3$) |
|---|---|
| 1 | 2.31(s, 3H), 3.75(s, 3H), 3.87(s, 3H), 5.89(d, J=11.8Hz, 1H), 6.87(d, J=11.8Hz, 1H), 7.05(d, J=6.6Hz, 1H), 7.27 (d, J=8.8Hz, 1H) |
| 2 | 1.87(brs, 3H), 1.97(brs, 3H), 2.25(s, 3H), 3.67(s, 3H), 3.87(s, 3H), 7.12(d, J=6.6Hz, 1H), 7.28(d, J=8.8Hz, 1H) |
| 3 | 1.89(brs, 3H), 2.13(brs, 3H), 3.74(s, 3H), 3.90(s, 3H), 7.01(d, J=9.2Hz, 1H), 7.12~7.70(m, 6H) |
| 4 | 1.67(d, J=6.6Hz, 3H), 1.82(brs, 3H), 1.91(brs, 3H), 2.2 2(s, 3H), 2.45(d, J=2.0Hz, 1H), 3.71(s, 3H), 4.80(dq, J= 6.6, 2.0Hz, 1H), 7.22(d, J=9.0Hz, 1H), 7.27(d, J=7.0Hz, 1H) |

A herbicide of the present invention containing N-acyl-N-phenylmaleamic acid derivatives [I] as the effective components, which are compounds of the present invention, has a superior herbicidal activity against various weeds causing problems upon the submerged soil treatment in paddy fields, such as gramineous weeds such as nobie (barnyardgrass, Echinochloa spp.), broad-leaved weeds such as azena (flase pimpernel, Lindernia pyxidaria), kikashigusa (toothcup, Rotala indica), mizohakobe (waterwort, Elatine triandra), cyperaceous weeds such as tamagayatsuri (small-flowered umbrellaplant, Cyperus difformis) and hotarui (bulrush, Scirpus juncoides), and weeds such as konagi (Monochoria vaginalis). Furthermore, the herbicide has a superior herbicidal activity against various weeds causing problems upon the foliage treatment and the soil treatment in uplands, such as broad-leaved weeds such as karashina (indian mustard, Brassica juncea), aobiyu (slender amaranth, Amaranthus viridis), hakobe (chickweed, Stellaria media ), shiroza (common lambsquarters, Chenopodium album), onamomi (heartleaf cocklebur, Xanthium strumarium), maruba-asagao (tall morningglory, Ipomoea purpurea), yaemugura (catchweed bedstraw, Galium aparine), suberihiyu (common purslane, Portulaca oteracea), ichibi (velvetleaf, Abutilon theophrasti), amerika-tsunokusanemu (hemp sesbania, Sesbania exaltata), ebisugusa (sicklepod, Cassia obtusifolia), inuhouzuki (black nightshade, Solanum nigrum), spedwells, smart weeds, violets, tade (Persicaria longiseta) and its relatives, and sumire (Viola mandshurica) and its relatives, gramineous weeds such as inubie (barnyardgrass, Echinochloa crus-galli), enokorogusa (green foxtail, Setaria viridis), karasumugi (wild oak, Avena fatua), mehishiba (henry crabgrass, Digitaria ciliaris), seibanmorokoshi (johnsongrass, Sorghum halepense) and enbaku (oat, Avena sativa), cyperaceous weeds such as kogomegayatsuri (rice flatsedge, cyperus iria) and hamasuge (nut grass, Cyperus rotundus), and commelinaceous weeds such as tsuyukusa (dayflower, Commelina communis). The herbicide of the present invention hardly injures major crops such as rice, wheat, corn and soybean.

Therefore, the herbicide of the present invention can be widely applied to upland, paddy field, orchard, pasture, turf, forest and non-crop land.

It is possible to process the herbicide of the present invention containing N-acyl-N-phenylmaleamic acid derivatives [I] which are the above compounds of the present invention as the effective components into an arbitrary form such as wettable powder, emulsion, granules, powder or flowable by using a pesticide adjuvant which is generally used in this field, such as an inactive solid carrier or liquid carrier and/or an emulsifying and dispersing agent and the like. As the inactive carriers, for example, talc, clay, bentonite, kaolin, diatomaceous earth, calcium carbonate, wood flour, starch, gum arabic, water, alcohol, kerosene, benzene, xylene, n-hexane, acetone, N,N-dimethylformamide, glycol ether, N-methylpyrrolidone can be cited.

Besides, it is possible to adequately incorporate auxiliary agents for formulation, such as spreader, diluent, surfactant and solvent.

Upon using N-acyl-N-phenylmaleamic acid derivatives [I] which are compounds of the present invention as a herbicide, a suitable application dosage is variable according to related factors such as manner of application, object of application, time of application and occurrence condition of weeds, but in general the application dosage, as expressed as the amount of the effective component, is preferably from 0.1 g to 300 g, and particularly preferably from 1 g to 300 g, per 10 ares. If it is not greater than 0.1 g, a sufficient herbicidal effect can not be obtained. If it is not less than 300 g, it becomes unfavorable because it not only is economically disadvantageous but also may cause the occurrence of phytotoxicity.

Furthermore, to use the herbicide containing N-acyl-N-phenylmaleamic acid derivatives [I] which are compounds of the present invention, it may be mixed with other herbicides, plant growth regulators, fungicides, insecticides, other pesticides, fertilizers and soil conditioners.

The following are Examples of herbicides according to the present invention, though compounds, carriers, adjuvants and the proportions of the ingredients are not limited to those in these examples. In these examples, the amount of each component is indicated by parts by weight.

EXAMPLE 2

(Wettable Powder)

| | |
|---|---|
| Compound No. 1 | 10 parts |
| Sodium lignin sulfonate | 1.5 parts |
| Polyoxyethylene alkylaryl ether | 1.5 parts |
| Clay | 87 parts |

These materials were mixed together until a uniform mixture was obtained, and the mixture was pulverized to obtain a wettable powder.

EXAMPLE 3

(Granules)

| | |
|---|---|
| Compound No. 1 | 7 parts |
| Bentonite | 30 parts |
| Sodium alkylsulfonate | 2 parts |
| Clay | 61 parts |

These materials were mixed together and kneaded until a uniform mixture was obtained, and the mixture was granulated by an ordinary granulation method thereby to obtain granules.

EXAMPLE 4

(Emulsion)

| | |
|---|---|
| Compound No. 1 | 5 parts |
| N-methylpyrrolidone | 44 parts |
| Solpol 7065 (product of Toho Kagaku Kogyo Co., Ltd.) | 43 parts |
| Solpol 355 (product of Toho Kagaku Kogyo Co., Ltd.) | 8 parts |

These materials were mixed together until a uniform mixture was obtained, thereby to obtain an emulsion.

The following experiments are illustrative of the herbicidal effects of N-acyl-N-phenylmaleamic acid derivatives [I] which are compounds of the present invention.

EXPERIMENT 1

(Flooded Soil Treatment)

Paddy soil (clay loam) was put into a pot so as to have a surface area of 1/15500 ares. Uniformly mixed seeds of several kinds of weeds, viz., nobie (barnyardgrass, Echinochloa spp.), broad-leaved weeds, hotarui (bulrush, Scirpus juncoides), tamagayatsuri (small-flowered umbrellaplant, *Cyperus difformis*) and konagi (monochoria, *Monochoria vaginalis*), were sown in the surface layer of the soil in each pot, and then paddy rice seedlings at the two- or three-leaved stage were transplanted into each pot to a depth of 2 cm, and water was fed into each pot so as to provide a 3 cm deep water layer on the soil surface. After 3 days, in other words, at the initial stage of germination of nobie (barnyardgrass, Echinochloa spp.), a predetermined amount of a selected compound in the form of diluted aqueous solution was dropped into the water layer in each pot. After that, the pots were kept in a glass chamber to allow the paddy rice and the weeds to grow, and after the lapse of 4 weeks from the treatment with the selected compounds, the herbicidal effects and the degree of injury to the paddy rice were evaluated. The results are shown in Table 3. In the table, the herbicidal effects and the degree of injury to the paddy rice are indicated by numerical values, which have the following meaning.

5: completely killed

4: seriously injured

3: considerably injured

2: somewhat injured

1: slightly injured 0.5: very slightly injured

0: not injured (normally grown)

EXPERIMENT 2

(Foliage Treatment)

Upon seedling stage (two- or three-leaved stage) of rice, cockspur (*Panicum crus-galli*), garden radish, aobiyu (slender amaranth, *Amaranthus viridis*) and mehishiba (henry crabgrass, *Digitaria cliaris*) which were grown on a cultivated soil put in pots of 1/15500 ares, a selected compound in suspended wettable powder was sprayed to each plant. After that, the pots were kept in a glass chamber to allow each plant to grow, and after the lapse of 4 weeks from the treatment with the selected compounds the herbicidal effects were evaluated. The results are shown in Table 4. The evaluation of the herbicidal effects was similarly conducted as to that of Experiment 1.

TABLE 3

| Compound No. | Quantity of Compound g/10a | Injury of Paddy | Herbicidal Effect |||||
|---|---|---|---|---|---|---|---|
| | | | nobie | broad-leaved weed | hotarui | tamagaya-tsuri | konagi |
| 2 | 6.25 | 0.5 | 5 | 5 | 4 | 5 | 5 |
|   | 3.125 | 0 | 4 | 4 | 3 | 5 | 5 |
| 3 | 6.25 | 0.5 | 5 | 5 | 5 | 5 | 5 |
|   | 3.125 | 0.5 | 5 | 5 | 5 | 5 | 5 |
| 4 | 6.25 | 1 | 5 | 5 | 5 | 5 | 5 |
|   | 3.125 | 0.5 | 5 | 5 | 4 | 5 | 5 |
| Comparative agent A | 6.25 | 0 | 4 | 4 | 4 | 5 | 5 |
|   | 3.125 | 0 | 2 | 3 | 1 | 5 | 5 |

Comparative agent-A: MO

TABLE 4

| Compound No. | Quantity of Compound g/10a | rice | cockspur | garden radish | aobiyu | mehishiba |
|---|---|---|---|---|---|---|
| 2 | 16 | 1 | 3 | 4 | 5 | 5 |
|   | 8 | 1 | 1 | 2 | 4 | 4 |
| 3 | 16 | 1 | 1 | 4 | 5 | 5 |
|   | 8 | 1 | 1 | 3 | 5 | 5 |
| Comparative agent B | 16 | 0 | 0 | 5 | 5 | 0 |
|   | 8 | 0 | 0 | 5 | 5 | 0 |

Comparative agent-B: Propanil

[INDUSTRIAL APPLICABILITY]

N-acyl-N-phenylmaleamic acid derivatives of the present invention, which are novel compounds, exhibit excellent herbicidal activity, and are useful as a herbicide which can be widely applied to upland, paddy field, orchard, turf, forest, non-crop land, etc., and which is not harmful to crops.

We claim:

1. An N-acyl-N-phenylmaleamic acid derivative represented by the general formula [I],

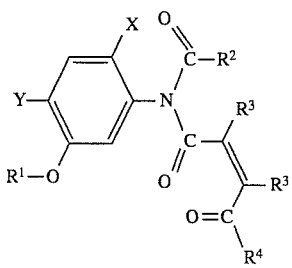

[I]

wherein X and Y each individually represent hydrogen atoms or halogen atoms, $R^1$ represents a hydrogen atom, a halogen atom, a lower alkyl group, a lower alkenyl group, a lower alkynyl group, a lower alkoxyalkyl group or a lower alkoxycarbonylalkyl group, $R^2$ represents a lower alkyl group, a halogenated lower alkyl group or a substituted or unsubstituted phenyl group, $R^3$ represents a hydrogen atom or a lower alkyl group, and $R^4$ represents a hydroxyl, a lower alkoxy group, a lower alkenyloxy group, a lower alkynyloxy group, a lower alkoxyalkoxy group, a benzyloxy group or a lower alkoxycarbonylalkoxy group.

2. A herbicide comprising, as an effective component, an N-acyl-N-phenylmateamic acid derivative which is represented by the general formula [I],

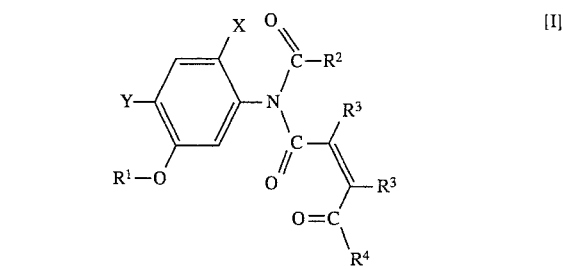

[I]

wherein X and Y each individually represent hydrogen atoms or halogen atoms, $R^1$ represents a hydrogen atom, a halogen atom, a lower alkyl group, a lower alkenyl group, a lower alkynyl group, a lower alkoxyalkyl group or a lower alkoxycarbonylalkyl group, $R^2$ represents a lower alkyl group, a halogenated lower alkyl group or a substituted or unsubstituted phenyl group, $R^3$ represents a hydrogen atom or a lower alkyl group, and $R^4$ represents a hydroxyl, a lower alkoxy group, a lower alkenyloxy group, a lower alkynyloxy group, a lower alkoxyalkoxy group, a benzyloxy group or a lower alkoxycarbonylalkoxy group.

3. A herbicide according to claim 2, which is in the form of a wettable powder comprising an inactive carrier.

4. A herbicide according to claim 2, which is in the form of granules comprising an inactive carrier.

5. A herbicide according to claim 2, which is in the form of an emulsion comprising an inactive carrier.

6. A herbicide according to claim 2, wherein said N-acyl-N-phenylmaleamic acid derivative is N-acetyl-N-(2-fluoro-4-chloro-5-methoxyphenyl)maleamic acid methyl ester.

7. A herbicide according to claim 2, wherein said N-acyl-N-phenylmaleamic acid derivative is N-acetyl-N-(2-fluoro- 4-chloro-5-methoxyphenyl)-2,3-dimethylmaleamic acid methyl ester.

8. A herbicide according to claim 2, wherein said N-acyl-N-phenylmaleamic acid derivative is N-benzoyl-N-(2-fluoro-4-chloro-5-methoxyphenyl)-2,3-dimethylmaleamic acid methyl ester.

9. A herbicide according to claim 2, wherein said N-acyl-N-phenylmaleamic acid derivative is N-acetyl-N-[2-fluoro-4-chloro-5-(1-methylpropargyloxy)phenyl]-2,3-dimethylmaleamic acid methyl ester.

* * * * *